United States Patent [19]

Langhals et al.

[11] Patent Number: 5,650,513

[45] Date of Patent: Jul. 22, 1997

[54] PROCESS FOR PREPARING PERYLENE-3,4-DICARBOXYLIC ACID DERIVATIVES, THE DERIVATIVES THUS PREPARED AND THEIR USE

[75] Inventors: Heinz Langhals, Ottobrunn; Leonhard Feiler, Riemerling, both of Germany

[73] Assignee: Ciba-Geigy Corporation, Tarrytown, N.Y.

[21] Appl. No.: 337,917

[22] Filed: Nov. 10, 1994

[30] Foreign Application Priority Data

Nov. 12, 1993 [CH] Switzerland .................. 3401/93

[51] Int. Cl.⁶ .................. C07D 221/18; C07D 401/04; C07D 407/04; C07D 409/04
[52] U.S. Cl. .................. 546/38; 544/330; 544/332; 544/336; 544/238; 544/326
[58] Field of Search .................. 546/38

[56] References Cited

U.S. PATENT DOCUMENTS

| | | | |
|---|---|---|---|
| 3,557,233 | 1/1971 | Zweig et al. | 260/668 |
| 4,714,666 | 12/1987 | Wiedemann et al. | 430/59 |
| 5,405,962 | 4/1995 | Muellen et al. | 546/27 |

FOREIGN PATENT DOCUMENTS

| | | | |
|---|---|---|---|
| 595292 | 5/1994 | European Pat. Off. | |
| 486491 | 11/1929 | Germany . | |
| 2512516 | 1/1985 | Germany . | |
| 4236885 | 10/1992 | Germany . | |
| 272528 | 10/1928 | United Kingdom . | |
| 1425716 | 2/1976 | United Kingdom | C09B 57/00 |

OTHER PUBLICATIONS

Nagas, Y. et al. *Chemical Abstracts*, vol. 115, No. 116288 (1991).
Mol. Cryst. Liq. Cryst., 1988, vol. 158B, pp. 337–352 Publication month not provided.
Chemical Abstract 85:209285 Publication month not provided.
Bull. Chem. Soc. Jpn. 1979, vol. 52, pp. 1723–1726 Publication month not provided.
Bull Chem. Soc. Jpn., 1981, vol. 54, pp. 1575–1576 Publication month not provided.
Chem. Ber., 1991, vol. 124, pp. 529–535 Publication month not provided.
Chem. Abstr. 86:31008p Publication month not provided.
Beilstein, EIII7, 4523, 4526 Publication month not provided.
Dyes & Pigm., 1991, vol. 16, pp. 19–25 Publication month not provided.
Goehring, R.R. et al. *J. Med. Chem.* 33, 926–931 (1990).

*Primary Examiner*—Mukund J. Shah
*Assistant Examiner*—King Lit Wong
*Attorney, Agent, or Firm*—Michele A. Kovaleski

[57] ABSTRACT

Reacting the industrially readily available perylene-3,4,9,10-tetracarboxylic dianhydride (3) with specific primary amines in the presence of water gives perylene-3,4-dicarboxylic bisimides (2). Their hydrolysis affords the perylene-3,4-dicarboxylic anhydride on a preparative scale, and this anhydride is reacted with any primary amines to give likewise the corresponding imides 2. Condensation of the anhydride with diamines results in novel types of dyes, namely perylene-3,4-dicarboxamidines which have very good fastness properties. Also claimed are specific perylene-3,4-dicarboxylic diesters, perylene-3,4-dicarboxylic ester amides, perylene-3,4-dicarboxamidines and perylene-3,4-dicarbonyl derivatives, processes for preparing these compounds and their use. The compounds according to the invention are suitable, for example, as colorants for the mass coloration of high-molecular-weight organic material, for use in security printing, as fluorescent dyes for machine-readable markings, as laser dyes, and for preparing non-impact printing toners, color filters, organic photoreceptors, electroluminescence and photoluminescence elements or sun collectors and in specific substituted compounds are also suitable for use as rheology improvers.

6 Claims, No Drawings

PROCESS FOR PREPARING PERYLENE-3,4-DICARBOXYLIC ACID DERIVATIVES, THE DERIVATIVES THUS PREPARED AND THEIR USE

The present invention relates to a process for preparing perylene-3,4-dicarboxylic acid derivatives, to the novel derivatives thus prepared, and to their use as highly lightfast fluorescent dyes.

While the perylene dyes, perylene-3,4,9,10-tetracarboxylic bisimides (1) have been employed for a long time as highly lightfast vat dyes and pigments and more recently also as fluorescent dyes in homogeneous solution, (see, for example, H. Zollinger, Color Chemistry, VCH Verlagsgesellschaft, Weinheim, 1987), astonishingly only a few specific representatives of the perylene-3,4-dicarboximides (2) are known.

While a general synthetic route to 1 is available by condensing the industrially prepared perylene-3,4,9,10-tetracarboxylic dianhydride (3) with primary amines, no preparative route to the analogous perylene-3,4-dicarboxylic anhydride (4) is available; 4 has only been obtained via gas-phase decarboxylation of 3 in insignificant amounts (Z. Iqbal, D. M. Ivory, H. Eckhardt, Mol. Cryst. Liqu. Cryst. 1988, 158b, 337).

In order to prepare the small number of known N-substituted derivatives of 2, an indirect route had to be selected which, however, severely restricts the selection of substituents on the imide nitrogen. To this end, first the unsubstituted perylene-3,4-dicarboximide 2a known since 1929 (DE-PS 486,491) was sulfonated and the sulfonated product was hydrolyzed to give the sulfonated perylene-3,4-dicarboxylic anhydride 6. 6 can be condensed with short-chain (sufficiently hydrophilic), aliphatic amino-terminated amines to give sulfonated dicarboximides (7). The corresponding dyes (2) are prepared by desulfonation in semi-concentrated sulfuric acid. The severe conditions necessary for this reaction, which may lead to sulfonations and eliminations, and the problems during preparative purification of sulfonated perylene derivatives severely limit the process, as a result of which only substances containing the radicals (hydrogen) methyl, ethyl, 1-propyl, 1-butyl, isobutyl, 1-pentyl, 1-hexyl, 1-octyl, 2-hydroxyethyl, phenyl, p-tolyl and p-anisyl have been prepared until now (Y. Nagao, T. Misono, Chem. Abstr. 85:20928s; Y. Nagao, T. Misono, Bull. Chem. Soc. Japan, 1979, 52, 1723; Y. Nagao, T. Misono, Bull. Chem. Soc. Jpn. 1981, 54, 1575). An attempt to prepare N-substituted perylene-3,4-dicarboximides containing various substituents on the nitrogen, for example the compound 2c below, from the perylene-3,4,9,10-tetracarboxylic 3,4-anhydride-9,10-imides which in the meantime are readily available by preparative methods (H. Kaiser, J. Lindner, H. Langhals, Chem. Ber. 1991, 124, 529) using the method described in Bull. Chem. Soc. Jpn. 1981, 54, 1575 for a small number of the abovementioned simple imides by decarboxylation gave only low yields (not more than 4%), therefore this method is not a general synthetic route to 2 either.

Condensation of perylene-3,4,9,10-tetracarboxylic dianhydride 3 with primary amines usually gives the corresponding perylenetetracarboxylic bismide 1 in high yields. However, if the condensation is carried out in the presence of water at high temperatures under pressure and in the presence of specific reagents, astonishingly monoimides 2 are also obtained in addition to the expected bisimides 1

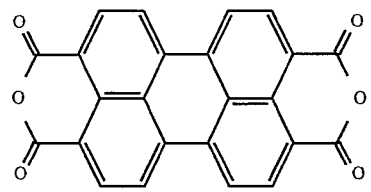

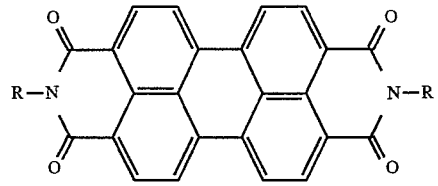

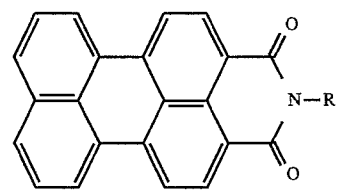

Accordingly, the invention provides a process for preparing perylene-3,4-dicarboximides of the formula I

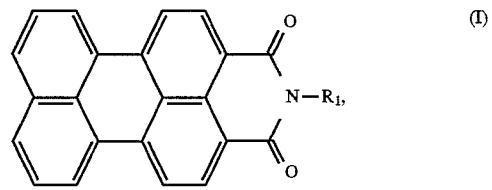

in which $R_1$ is an alkyl, aralkyl or cycloalkyl group or a carbocyclic or heterocyclic aromatic radical, by reacting perylene-3,4,9,10-tetracarboxylic dianhydride with a primary amine $R_1$—$NH_2$ at a temperature of 150°–350° C. and under pressure, in the presence of water and in the presence of a zinc salt, lead salt, calcium salt or magnesium salt and of a nitrogen-containing heterocycle as the base. The preferred temperature range is about 180°–250° C. A particularly suitable reaction temperature is also 190° C. or 210°–220° C.

Particularly suitable salts for carrying out the process according to the invention are lead acetate, zinc chloride and, in particular, zinc acetate.

Particularly suitable nitrogen-containing heterocycles are quinoline, pyridine and, in particular, imidazole. Preferably, the reaction is carried out using the particular heterocyclic compound as the solvent.

The reaction proceeds particularly smoothly with primary amines containing a sterically hindered, preferably solubilizing, organic radical $R_1$. Particularly suitable radicals $R_1$ include, in particular, the following: 2,5-di-tert-butylphenyl, 2,5-di-tert-butyl-4-nitrophenyl, 4-tert-butylphenyl, 2,3-dimethylphenyl, 1-hexylheptyl, 1-octylnonyl, 1-nonyldecyl, cyclopropyl, cyclopentyl, cyclohexyl, cycloheptyl, cyclooctyl, cyclododecyl, adamantyl or 4-carbamoylphenyl.

The optimum amount of the water added for the reaction according to the invention, of the primary amine $R_1$-$NH_2$ or of the salt used can vary from case to case. When preparing the monoimide 2b ($R_1$ is 2,5-di-tert-butylphenyl) from the dianhydride 3, it is convenient to use about 0.7 ml of water/mmol of 3, about 1.6 mol of 2,5-di-tert-butylaniline/mol of 3 and about 135 mg of zinc acetate/mmol of 3.

Under these conditions, compound 2b is obtained in an isolated yield of about 50%. The remainder is essentially unreacted starting material, perylene and the corresponding bisimide 1b, which can be easily separated off by chromatography. The optimum reaction temperature is about 190° C. At higher temperatures higher proportions of perylene are obtained, and at lower temperatures the yield decreases. For workup, it may be advantageous to carry out the reaction at the higher temperature of 210-220° C. and to employ a shorter reaction time of about 7-8 h. Although the yield in this case is somewhat lower and also more perylene is formed, which however can be separated off very easily by chromatography, the corresponding bisimide 1b, which is somewhat more difficult to separate off, is hardly formed at all.

At a yield of 50% in the reaction in the autoclave, monoimide 2b is a suitable starting material for preparing perylene-3,4-dicarboxylic anhydride 4. To this end, 2b is reacted, for example, with KOH in tert-butyl alcohol, followed by hydrolysis to give the monoamide of perylene-3,4-dicarboxylic acid. Acidification of the alkaline solution of the monoamide thus obtained results in further hydrolysis of a portion thereof to give the desired perylene-3,4-dicarboxylic anhydride (4) (while the other portion reverts to the starting material 2b). A particularly suitable acid is 50 per cent acetic acid, which gives yields of more than 60% of 4; based on conversion, the isolated yield of 4 is even more than 90%. The remaining portion of the cyclization product 2b can be separated off without any difficulty by dissolution with hot potassium carbonate solution, filtration and precipitation with acetic acid, so that the anhydride 4 is obtained in high purity.

The anhydride 4 thus obtained can be condensed with any primary amines under the above described reaction conditions, for example using zinc acetate in imidazole or quinoline, to give the perylene-3,4-dicarboximides (2).

Accordingly, the invention also provides a process for preparing perylene-3,4-dicarboximides of the formula I given above by reacting perylene-3,4-dicarboxylic anhydride with a primary amine $R_1$-$NH_2$ at a temperature of 150°–350° C. and under pressure in the presence of a zinc salt, lead salt, calcium salt or manganese salt and of a nitrogen-containing heterocycle as the base.

The invention also provides a process for preparing perylene-3,4-dicarboximides of the formula I given above by reaction of perylene-3,4-dicarboximide with a, preferably primary, alkyl halide $R_1$-X, preferably with an alkyl bromide or alkyl iodide, at a temperature of, preferably, 20°–100° C., in the presence of a strong base. Particularly suitable bases are alcoholates or hydroxides, in particular sodium methoxide or potassium hydroxide. When KOH powder is used, suitable solvents for deprotonation are aprotic solvents, such as, in particular, dimethyl sulfoxide, while the use of sodium methoxide makes it possible also to use alcohols, in particular methanol. Particularly suitable solvents for alkylation are aprotic polar solvents, such as, in particular, dimethyl sulfoxide or N-methylpyrrolidone.

The perylene-3,4-dicarboximides (2) prepared by the two processes according to the invention defined above are, with few exceptions, still novel compounds.

Accordingly, the invention also relates to novel perylene-3,4-dicarboximides of the formula II

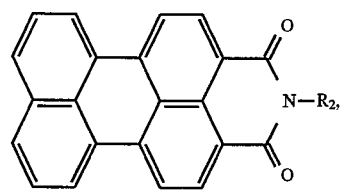

in which $R_2$ is an alkyl group having at least 9 C atoms or cycloalkyl, aralkyl, a heterocyclic aromatic radical or a carbocyclic aromatic radical having a total of at least 8 C atoms.

The perylene-3,4-dicarboximides (2) and perylene-3,4-dicarboxylic anhydride (4) which have been described above and are now readily available can be used to prepare a multitude of perylene-3,4-dicarboxylic acid derivatives without difficulty using generally known reactions.

Accordingly, the invention also relates to perylene-3,4-dicarboxylic diesters of the formula III

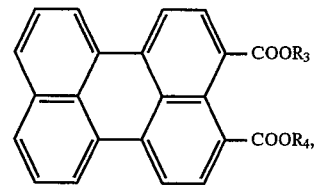

in which $R_3$ and $R_4$ are, independently of one another, an alkyl, aralkyl or cycloalkyl group or a carbocyclic or heterocyclic aromatic radical. These compounds can be prepared, for example, by hydrolysis of a monoimide or of the monoanhydride, followed, for example, by alkylation of the hydrolysis product. Thus, anhydride 4 can be reacted with sodium methoxide and methyl iodide (or else dimethyl sulfate) (see also DE-A 2,512,516) or, for example, with propyl bromide and potassium t-butoxide in N-methylpyrrolidone to give the dimethyl ester or the di-n-propyl ester. These esters form yellow solutions having an intensive yellow-green fluorescence.

Of interest are also perylene-3,4-dicarboxylic acid and alkali metal salts and alkaline earth metal salts thereof, for example potassium salts, sodium salts, magnesium salts, calcium salts or strontium salts.

The invention also relates to perylene-3,4-dicarboxylic ester amides of the formula IV $$\text{(IV)}$$

[structure with $CON(R_5)_2$ and $COOR_6$ groups on perylene]

in which the two $R_5$ are identical or different and in which $R_5$ and $R_6$ are, independently of one another, H, an alkyl, aralkyl or cycloalkyl group or a carbocyclic or heterocyclic aromatic radical. These compounds can be prepared, for example, by partial hydrolysis of a perylene-3,4-dicarboximide as defined, followed, if desired, by alkylation or arylation of the product thus obtained.

The invention also relates to perylene-3,4-dicarboxamides of the formula V

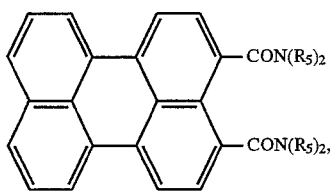

(V)

in which the two $R_5$ are identical or different and are H, an alkyl, aralkyl or cycloalkyl group or a carbocyclic or heterocyclic aromatic radical. These products can be prepared, for example, by partial hydrolysis of a perylene-3,4-dicarboximide as defined, followed by reaction of the product with a suitable amine.

The invention also provides a process for preparing perylene-3,4-dicarbonyl derivatives of the formula VI

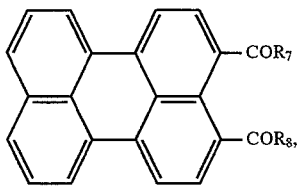

(VI)

in which $R_7$ and $R_8$ are, independently of one another, H, an alkyl, aralkyl or cycloalkyl group or a carbocyclic or heterocyclic aromatic radical, by reduction of the perylene-3,4-dicarboxylic acid or by reduction of the diesters of the formula III described above, followed by reaction with C nucleophiles. Only a few dicarbonyl derivatives of the formula VI have so far been described, and the known derivatives (cf. Beilstein, E III 7, 4523 and 4526) have been prepared by Friedel-Crafts acylation of perylene.

Accordingly, the invention also relates to novel perylene-3,4-dicarbonyl derivatives of the formula VI, in which $R_7$ and $R_8$ are as defined above, with the proviso that $R_7$ and $R_8$ are not simultaneously phenyl, p-tolyl or 4-chlorophenyl.

The reaction of the perylene-3,4-dicarboxylic anhydrides as defined with primary diamines leads to further novel compounds, namely perylene-3,4-dicarboxamidines of the formula VII

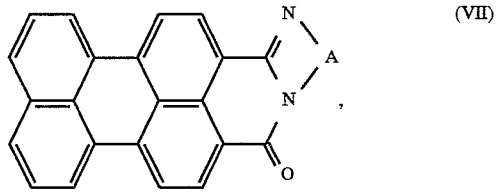

(VII)

in which A is $C_5$-$C_7$cycloalkylene, phenylene, naphthylene, pyridylene, a polyfused aromatic carbocyclic or heterocyclic radical or a divalent radical of the formula VIII, IX or X

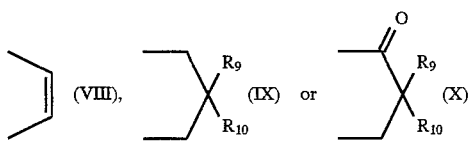

where A can be substituted by halogen, alkyl, cyano or nitro and $R_9$ and $R_{10}$ are, independently of one another, $C_1$-$C_4$alkyl, phenyl or 4-tolyl, which are also provided by the invention.

Preferred peryleneamidines of the formula VII are compounds in which A is 1,2-cyclopentylene, 1,2-cyclohexylene, 1,2-phenylene, 2,3- or 1,8-naphthylene, 2,3- or 3,4-pyridylene, 9,10-phenanthrylene or a divalent radical of the formula VIII, IX or X, and in particular those in which A is 1,2-phenylene, 1,8-naphthylene or a divalent radical of the formula VIII, XI or XII

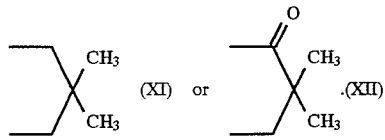

The invention also provides a process for preparing peryleneamidines of the formula VII by reacting perylene-3,4-dicarboxylic anhydride with a primary diamine of the formula XIII $$H_2N-A-NH_2 \qquad (XIII),$$

where A is as defined above, with the proviso that A is not a radical of the formula VIII.

The invention also provides a process for preparing peryleneamidines of the formula VII in which A is a radical of the formula VIII by reacting a substituted or unsubstituted imidazole with perylene-3,4-dicarboxylic anhydride. This reaction is preferably carded out in the presence of sterically hindered amines or in the presence of tertiary mines, for example 3-amino-3-ethylpentane or 2,6-di-tert-butylpytidine.

An alkyl as the radicals $R_1$ to $R_8$ defined above is preferably $C_1$-$C_{41}$alkyl. The radicals can be straight-chain or branched. Preference is given to secondary alkyl radicals for example 1-hexylheptyl, 1-heptyloctyl, 1-octylnonyl or 1-nonyldecyl.

Aralkyl radicals $R_1$ to $R_8$ are, for example, benzyl.

Cycloalkyl radicals $R_1$ to $R_8$ can be mono- or else polycyclic and preferably contain 3–12 carbon atoms in the ring. Examples of suitable radicals are cyclopropyl, cyclobutyl, cyclopentyl, cyclohexyl, cyclooctyl, cyclododecyl, decalinyl or adamantyl.

Carbocyclic or heterocyclic aromatic radicals $R_1$ to $R_8$ can also contain one or more fused or unfused rings which are preferably 5- or 6-membered. The heterocyclic aromatic radicals preferably contain one, two or three hetero atoms, in particular N, O or S atoms, in the ring. The carbocyclic aromatic radicals preferably contain 6–12 C atoms. Examples of suitable radicals are phenyl, tolyl, naphthyl or biphenyl. Examples of suitable heterocyclic aromatic radicals are furyl, thienyl, pyrrolyl, imidazolyl, pyrazolyl, isothiazolyl, isoxazolyl, pyridyl, pyrazinyl, pyrimidinyl, pyridazinyl, indolyl, isoindolyl, indazolyl, quinolyl, isoquinolyl, quinazolinyl or carbazolyl.

The perylene-3,4-dicarboxylic acid derivatives of the formulae I to VII according to the invention are preferably unsubstituted in the perylene ring system. However, they may also contain one or more, but usually at most six, substituents in the ring system, possible substituents being, independently of one another, alkyl, aralkyl, cycloalkyl, alkoxy, aryloxy, alkylaryl, alkylmercapto, arylmercapto, a carbocyclic or heterocyclic aromatic radical or chlorine, bromine, nitro, $-SO_3H$ (including metal salts or ammonium salts thereof) or $-SO_3R$ (where R is alkyl or aryl), amino, acylaminomethyl, for example acetylaminomethyl, alkylamino, arylamino, phthalimidomethyl, aminomethyl, dimethylaminomethyl (prepared, for example, by cleavage of the corresponding phthalimido derivative), pyrazolomethyl.

The last-mentioned sulfo- and amino-substituted perylene-3,4-dicarboxylic acid derivatives are suitable in particular as rheology improvers. Corresponding derivatives of other pigment systems, for example of phthalocyanine pigments or quinacridone pigments, and their preparation are disclosed, for example, in U.S. Pat. No. 4,981,888, EP-A 356,390, EP-A 508,704, U.S. Pat. No. 5,212,221 or EP-A 485,337. The present substituted perylene-3,4-dicarboxylic acid derivatives can be prepared analogously.

Preferably, the substituent is in the 1 or 9 position, and the substituents are in the 1,6; 1,9; 2,5; 7, 12; 8,11 or 9,10 positions. The substituted perylene derivatives preferably contain one or two substituents in the ring system, the substituents being preferably identical in disubstituted compounds.

The substituted perylene derivatives can be prepared from the corresponding unsubstituted compounds by generally known methods or else be synthesized by conversion of an already substituted different derivative (for example, substituted diesters from substituted imides). The preparations of the nitro, amino and bromo derivatives are described below by way of example.

The perylene dicarboximides (2) can be nitrated, for example, with various reagents. Reacting 2b (where $R_1$ is 2,5-di-tert-butylphenyl) with nitric acid in glacial acetic acid leads to a multitude of products, of which the 1,6-dinitro derivative can be isolated without difficulty by chromatography in a yield of 13%.

When 2c (where $R_1$ is 1-hexylheptyl) is reacted with nitric acid in acetic anhydride, 8 % of the 1-nitro derivative, 35% of the 1,9-dinitro derivative and 14% of the 9,10-dinitro derivative can be isolated by chromatography.

Nitration of 2c with $N_2O_4$ in methylene chloride produces a complex reaction mixture from which 7% of the 1-nitro compound can be separated off by chromatography. Catalysis of the reaction by methanesulfonic acid favours a second substitution. In this case, 12% of the 1,6-dinitro, 36% of the 9-nitro, 9 % of the 2,5-dinitro and 25% of the 9,10-dinitro substitution product are found.

Nitration of 2c by $N_2O_4$ in methylene chloride is strongly influenced by light. Owing to the broad light absorption of 2c in the visible region, normal daylight is already completely sufficient for this, and the photoreactions proceed at high quantum yields.

When nitration of 2c with $N_2O_4$ in methylene chloride is carded out in complete darkness, the reaction product which can be isolated is 55% of the 9-nitro derivative as pure substance, the remainder being almost exclusively unreacted starting material, which can be easily separated off. Accordingly, this reaction is the best method of preparing the 9-nitro derivative on a preparative scale.

The 9-nitro compound can be reduced with iron in glacial acetic acid to the 9-amine, 30% of which is obtained directly. A further 20% can be isolated by a chromatographic workup of the residues. Better results are obtained in the reduction with iron in hydrochloric acid. This method allows direct isolation of the amine in 85% yield.

In contrast to the perylene dyes 1, the abovementioned 9-amine remarkably has a strong positive solvatochromic effect. Its absorption maximum is shifted from 554 nm in chloroform to as much as 602 nm in methanol. Since the dye is relatively lightfast and in addition weakly fluorescent, it is of interest for producing the third harmonic wave in non-linear optics via a resonance effect.

Derivatization of 2c with bromine (cf. also Y. Nagao, Y. Abe, T. Misono, Dyes. Pigm. 1991, 16, 19) in chlorobenzene gives the 9-bromo derivative in 63% yield in addition to polybrominated products. This reaction is thus analogous to nitration in the absence of light. 2b can be brominated by the same method. However, the reaction also produces polybrominated 2b which could not be separated off. In contrast, carrying out the bromination in chlorobenzene in the presence of potassium carbonate enables 77% of 9-bromo-2b to be isolated.

The perylene-3,4-dicarboxylic acid derivatives of the formulae I to VII according to the invention show very strong fluorescence in solution, which occurs at high quantum yields. The lightfastness is even superior to that of the perylene dyes (perylenebisimides 1 above), which are known for being extremely photostable and which at present are the most stable fluorescent dyes of all. Thus, for example, the rate at which monoimide 2b bleaches in dimethylformamide solution is slower by a factor of 20 than that of 1b. Similar results are found for the other dyes 2. In general, the solubility of the dyes is higher than that of the corresponding perylene dyes 1. The relatively narrow absorption and fluorescence band of the compounds according to the invention results in brilliant shades. The almost rectangular-shaped absorption band is favourable for a high colour strength.

As solids, the compounds according to the invention form bright red pigments which surprisingly also exhibit intensive fluorescence as solids. Accordingly, they are also of interest as lightfast fluorescent pigments. In general, well-ordered crystallites give in each case an intensive, long-wave fluorescence band. In contrast, when the substance is very finely pulverized or rapidly precipitated from a solution, the fluorescence of shorter wavelength becomes the band of highest intensity, and the spectrum of the solid is more like the fluorescence spectrum of solutions but has undergone a slight hypsochromic shift with respect to the latter.

Compared with the peryleneimide dyes, the fluorescence of the peryleneamidines of the formula VII has been shifted to longer wavelengths. As solids, these substances also form red pigments.

By virtue of their properties, the compounds according to the invention are suitable for a multitude of applications.

Thus, for example, they can be used as pigments for the mass coloration of plastics or coatings and paints. Accordingly, the invention also relates to mass-coloured high-molecular-weight organic material containing a compound of the formula I to VII and a process for mass-colouring high-molecular-weight organic material using these compounds.

Examples of suitable plastics are polyolefins, polyvinyl chloride, fluoro polymers, for example polyfluoroethylene, polytrifluorochloroethylene or tetrafluoroethylene/hexafluoropropylene copolymers, silicone resins, but in particular engineering plastics, for example polycarbonates, polylacrylates, polymethacrylates, polystyrene, ABS, polyesters, in particular polyalkylene terephthalates, such as polybutylene terephthalate (PBT) or polyethylene terephthalate (PET), polyamides, polyether ketones, polyurethanes, individually or in mixtures. Advantageously, the compounds according to the invention are used in a concentration of 0.01 to 10, preferably 0.01–5, % by weight, relative to the polymer.

Examples of polyolefins which can be coloured with the compounds according to the invention include polyethylene of high and low densities (HDPE, LDPE and LLDPE), polyisobutylene and, in particular, polypropylene, and copolymers of polyolefins with, for example, polyethers, polyether ketones or polyurethanes. Preference is given to polypropylene.

Coloration takes place by customary methods, for example by mixing a compound according to the invention or a mixture of such compounds with the plastic granules or powder without the need of prior incorporation into a preparation and extruding the mixture to give fibres, films or granules. The latter can then be moulded, for example in an injection moulding process, to give articles.

The red fluorescent colorations obtained exhibit high purity and high saturation and are distinguished by good transparency and by good resistance, in particular to light.

The invention also relates to the use of the compounds according to the invention in security printing, as fluorescent dyes for machine-readable markings, as laser dyes, and for preparing non-impact printing toners, colour filters, organic photoreceptors, electroluminescence and photoluminescence elements or sun collectors.

Compounds according to the invention containing one or more substituents selected from the group consisting of —$SO_3H$ (including metal salts or ammonium salts thereof) or —$SO_3R$ (where R is alkyl or aryl), amino, acylaminomethyl, for example acetylaminomethyl, alkylamino, arylamino, phthalimidomethyl, aminomethyl, dimethylaminomethyl (prepared, for example, by cleaving the corresponding phthalimido derivative) or pyrazolomethyl can furthermore be used as rheology improvers.

The examples which follow illustrate the invention.

EXAMPLES 1–4

Preparation of Perylenedicarboximides from Perylenetetracarboxylic Dianhydride in an Autoclave

Example 1

N-(2,5-Di-t-butylphenyl)perylene-3,4-dicarboximide (2b)

In an autoclave of capacity 100 ml, a mixture of 3.66 g (9.34 mmol) of perylene-3,4,9,10-tetracarboxylic dianhydride, 18.7 g of imidazole, 1.32 g of zinc acetate dihydrate, 8.0 ml (450 mmol) of water and 1.05 g (5.12 mmol) of 2,5-di-tert-butylaniline (prepared according to Rec. Trav. Chim. Pays-Bas, 1958, 77, 491) is heated at 210° C. for 23 h. After the end of the reaction, the mixture is removed from the autoclave by rinsing with ethanol, treated with water and concentrated hydrochloric acid and boiled until all the ethanol has evaporated. The brown-red residue is filtered off with suction and boiled in 10 per cent potassium carbonate solution for 1 h. The residue is filtered off with suction, dried at 120° C. in a drying cabinet and chromatographed on silica gel using chloroform. This gives a forerun (yellow, blue fluorescence) of perylene, followed by N-(2,5-di-tert-butylphenyl)perylene-3,4-dicarboximide (2b) and then by N,N'-bis(2,5-di-tert-butylphenyl)perylene-3,4,9,10-tetracarboximide (1b). Yield 2.40 g (50.5%), m.p. >300° C. $R_f$ (CHCl$_3$/silica gel)=0.85. UV (CHCl$_3$): $\lambda_{max}$ ($\epsilon$)=489 nm (35300), 512 (33590). Fluorescence (CHCl$_3$, exc. 489 nm) $\lambda_{max}$ ($I_{rel}$)=535 nm (1), 576 nm (0.36).

| $C_{36}H_{31}NO_2$ (509.7) | Calculated | C 84.84 | H 6.13 | N 2.75 |
|---|---|---|---|---|
| | Found | C 84.79 | H 6.35 | N 2.81 |

Example 2

N-(4-t-Butylphenyl)perylene-3,4-carboximide from perylene-3,4,9,10-tetracarboxylic dianhydride 3.66 g (9.33 mmol) of perylene-3,4,9,10-tetracarboxylic dianhydride are mixed with 18.66 g of imidazole, 1.36 g of zinc acetate dihydrate, 8 ml of water and 1.89 g (12.7 mmol) of 4-t-butylaniline, and the mixture is heated in an autoclave at 220° C. for 10 h. The reaction product is removed from the autoclave by washing with ethanol, treated with 200 ml of 10% hydrochloric acid and boiled until no more ethanol is present. The precipitate is filtered off with suction and then boiled in 10% potassium carbonate solution. The insoluble residue is filtered off with suction, washed with water and dried at 120° C. in a drying cabinet. Chromatography of the residue on silica gel using chloroform allows isolation of 2 products having $R_f$ values of 0.40 and 0.19, which can be identified by $^1$H NMR spectroscopy as N-(4-t-butylphenyl)perylene-3,4-dicarboximide and N,N'-di(4-t-butylphenyl)perylene-3,4,9,10-bis(carboximide). Owing to the poor solubility of the products in chloroform, only a small portion of the crude product is purified by chromatography, and the overall yield is obtained by extrapolation of the amounts obtained. This gives about 10% of N-(4-t-butylphenyl)perylene-3,4-dicarboximide and about 30% of N,N'-di(4-t-butylphenyl)perylene-3,4,9,10-bis(carboximide).

Example 3

N-(1-Hexylheptyl)perylene-3,4-dicarboximide (2c)

1.2 g (3.1 mmol) of perylene-3,4,9, 10-tetracarboxylic dianhydride, 6.2 g of imidazole, 470 mg (2.36 mmol) of 7-aminotridecane (prepared according to J. Prakt. Chem. 1980, 322, 261), 150 mg (0.68 mmol) of zinc acetate dihydrate and 3.0 ml (170 mmol) of water are heated in an autoclave (100 ml) at 190° C. for 24 h. Workup is analogous to that used in the preparation of 2b. Yield 1.25 g (27%).

Example 4

N-(1-Octylnonyl)perylene-3,4-dicarboximide (2d)

1.4 g (3.1 mmol) of perylene-3,4,9,10-tetracarboxylic dianhydride, 6.1 g of imidazole, 960 mg (3.7 mmol) of 9-aminoheptadecane (prepared according to DE-A 4,007, 618), 150 mg (0.68 mmol) of zinc acetate dihydrate and 3.0 ml (170 mmol) of water are heated in an autoclave (100 ml) at 190° C. for 24 h. Workup is analogous to that used for preparing 2b. Yield 130 mg (7% by extractive recrystallization from methanol, such as described in Chem. Ber. 1985, 118, 4641) orange red crystals showing strong solid fluorescence, m.p. 143°–143.6° C. $R_f$ (CHCl$_3$/silica gel)= 0.94. UV (CHCl$_3$): $\lambda_{max}$ ($\epsilon$)=454 nm (sh, 17620), 485 (32530), 508 (29480). Fluorescence (CHCl$_3$, exc. 485 nm): $\lambda_{max}$ ($I_{rel}$)=572 (sh, 0.49), 536 (1).

| $C_{39}H_{45}NO_2$ (559.8) | Calculated | C 83.68 | H 8.10 | N 2.50 |
|---|---|---|---|---|
| | Found | C 83.62 | H 8.02 | N 2.73 |

EXAMPLES 5–13

Preparation of Perylenedicarboximides from Perylenedicarboxylic Anhydride

Example 5

N-(1-Hexylheptyl)perylene-3,4-dicarboximide (2c)

200 mg (620 mmol) of perylene-3,4-dicarboxylic anhydride (prepared according to Example 20, below) are heated together with 250 mg (0.12 mmol) of 7-aminotridecane, 110 mg of zinc acetate dihydrate and 1.2 g of imidazole under an argon inert atmosphere at 135°–140° C. for 1 h. After cooling, the dark-red melt cake is digested with 100 ml of ethanol, and 100 ml of 15 per cent hydrochloric acid are added to the resulting suspension, and the mixture is boiled until all the ethanol has evaporated (the reaction product is readily soluble in ethanol). The solid is filtered off with suction and washed with warm water until the filtrate run-off no longer gives a yellow fluorescence. The crude product is then dried in a drying cabinet at 120° C. for 2 h and then chromatographed on silica gel using chloroform. The first coloured fraction is recrystallized by extraction with methanol. Yield 200 mg (63%) orange-red crystals showing strong solid fluorescence, m.p. 166°–168° C. $R_f$ (chloroform/silica gel)=0.87. UV (CHCl$_3$): $\lambda_{max}$ ($\epsilon$)=506 (30250), 484 (31580). Fluorescence (CHCl$_3$, exc. 506 nm) $\lambda_{max}$ ($I_{rel}$): 540 (1), 568 (0.52).

| $C_{35}H_{27}NO_2$ (503.7) | Calculated | C 83.50 | H 7.36 | N 2.78 |
|---|---|---|---|---|
| | Found | C 83.58 | H 7.28 | N 2.92 |

Example 6

N-(1-Nonyldecyl)perylene-3,4-dicarboximide (2e)

230 mg (0.70 mmol) of perylene-3,4-dicarboxylic anhydride are reacted with 400 mg (1.40 mmol) of 10-aminononadecane (prepared according to DE-A 4,007,618) and 1.0 g of imidazole under an argon inert atmosphere as in 2c, followed by workup. After chromatography on silica gel using chloroform, the reaction product is applied to silica gel using petroleum ether, and the purely aliphatic by-products are washed off with about 1 l of petroleum ether. The reaction product is then eluted with toluene, and is then recrystallized by extraction with pentane. Yield 400 mg (85%), m.p. 143°–143.5° C. $R_f$(silica gel/CHCl$_3$)=0.94. UV (CHCl$_3$): $\lambda_{max}$ ($\epsilon$)=507 nm (31319), 482 (32213), 453 (sh, 17450). Fluorescence (CHCl$_3$, exc. 507 nm) $\lambda_{max}$ ($I_{rel}$)=539 (1), 557 (0.47).

| $C_{41}H_{49}NO_2$ (587.8) | Calculated | C 83.77 | H 8.40 | N 2.38 |
|---|---|---|---|---|
| | Found | C 84.03 | H 8.47 | N 2.52 |

Example 7

N-Cyclooctylperylene-3,4-dicarboximide (2f)

300 mg (0.93 mmol) of perylene-3,4-dicarboxylic anhydride are reacted with 1.5 g (2.15 mmol) of cyclooctylamine and 3 g of imidazole under an argon inert atmosphere at 140° C. for 12 h as in 2c, and the reaction product is worked up and dried in a drying cabinet. To remove unreacted starting material, the product is boiled in 10 per cent potassium carbonate solution and washed with hot water until the filtrate run-off is colourless. The brown-red product is dried in a drying cabinet at 120° C. and then recrystallized by extraction with ethanol. Yield 290 mg (72%) of dark-red crystalline powder without solid fluorescence, m.p. 342°–343° C., $R_f$ (CHCl$_3$/silica gel)=0.78. UV (CHCl$_3$): $\lambda_{max}$ ($\epsilon$)=506 nm (32000), 484 (32100), 264 (35200). Fluorescence (CHCl$_3$) $\lambda_{max}$ ($I_{rel}$)=511 nm, 542 (1), 573 (sh, 0.51).

| $C_{30}H_{25}NO_2$ (431.5) | Calculated | C 83.50 | H 5.84 | N 3.25 |
|---|---|---|---|---|
| | Found | C 83.22 | H 5.83 | N 3.53 |

Example 8

N-Cyclododecylperylene-3,4-dicarboximide (2g)

190 mg (0.56 mmol) of perylene-3,4-dicarboxylic anhydride are reacted with 140 mg (1.28 mmol) of cyclododecylamine and 2.0 g of imidazole under an argon inert atmosphere as in 2c, and the reaction product is worked up. After chromatography on silica gel using chloroform, it is recrystallized by extraction with toluene. Yield 190 mg (66%), m.p. 285° C., $R_f$ (CHCl$_3$/silica gel)=0.58. UV (CHCl$_3$): $\lambda_{max}$ ($\epsilon$): 454 (shoulder, 19085), 484 (32630), 507 (32015). Fluorescence (CHCl$_3$, exc. 584 nm) $\lambda_{max}$ ($I_{rel}$)=538 (1), 572 (sh, 0.44).

| $C_{34}H_{33}NO_2$ (487.6) | Calculated | C 83.75 | H 6.82 | N 2.87 |
|---|---|---|---|---|
| | Found | C 83.75 | H 6.81 | N 2.91 |

Example 9

N-2-Hydroxyethylperylene-3,4-dicarboximide (2h)

190 mg (0.56 mmol) of perylene-3,4-dicarboxylic anhydride are reacted with 0.85 ml (1.40 mmol) of 2-aminoethanol and 1.18 g of imidazole under an argon inert atmosphere for 96 h as in 2c, and the reaction product is worked up and dried in a drying cabinet. To remove unreacted starting material, it is boiled in 10 per cent potassium carbonate solution and washed with hot water until the filtrate run-off is colourless. The brown-red product is dried in a drying cabinet at 120° C. and then recrystallized by extraction with toluene. Yield 50 mg (23%), m.p. >260° C. UV (CHCl$_3$): $\lambda_{max}$=489 nm, 509. Fluorescence (CHCl$_3$, exc. 489 nm) $\lambda_{max}$ ($I_{rel}$)=546 nm (1), 579 (sh, 0.46).

| $C_{24}H_{15}NO_3$ (365.4) | Calculated | C 78.89 | H 4.14 | N 3.83 |
|---|---|---|---|---|
| | Found | C 78.26 | H 4.27 | N 3.84 |

Example 10

N-(4-t-Butylphenyl)perylene-3,4-dicarboximide 0.70 g (2.17 mmol) of perylene-3,4-dicarboxylic anhydride is mixed with 0.49 g (3.28 mmol) of 4-t-butylaniline, 3.00 g of imidazole and 0.10 g of zinc acetate dihydrate and the mixture is heated at 140°–150° C. for 5 h. While still hot, the mixture is treated with 100 ml of ethanol, and then 200 ml of 10% hydrochloric acid are added. The red suspension is heated until all the ethanol has evaporated, and the product is then filtered off with suction. The red-brown residue is boiled in 10% potassium carbonate solution, the solid residue is filtered off with suction while hot and rinsed several times with hot dist. water. The red residue is dried in a drying cabinet at 120° C. and then recrystallized by extraction with a toluene/methanol mixture to give 0.80 g (81%) of red N-(4-t-butylphenyl)perylene-3,4-dicarboximide which shows a red solid fluorescence. M.p. >330° C. $R_f$(CHCl$_3$/silica gel)=0.35.

| $C_{32}H_{23}NO_2$ (453.5) | Calculated | C 84.74 | H 5.11 | N 3.09 |
| --- | --- | --- | --- | --- |
| | Found | C 84.58 | H 5.05 | N 3.16 |

Example 11

N-Cyclopentylperylene-3,4-dicarboximide 0.30 g (0.93 mmol) of perylene-3,4-dicarboxylic anhydride is mixed with 0.24 g (2.80 mmol) of cyclopentylamine and 3 g of imidazole, and the mixture is heated under nitrogen at 145° C. for 4 h. The reaction product is removed from the flask by washing with ethanol, and the mixture is then treated with 10% hydrochloric acid and boiled until no more ethanol is present. The precipitated product is filtered off with suction, boiled in potassium carbonate solution and the solid residue is filtered off with suction and washed with hot dist. water. 60 mg (20%) of perylene-3,4-dicarboxylic anhydride can be recovered by acidifying the filtrate with conc. hydrochloric acid. The red residue is recrystallized 3 times by extraction with methanol and then dried in a drying cabinet at 120° C. Yield 0.22 g (61%) of dark-red small needles showing a strong red solid fluorescence, m.p. >315° C. $R_f$ (CHCl$_3$/silica gel)=0.18. UV (CHCl$_3$): $\lambda_{max}$ ($\epsilon$)=506 (31013), 485 (31425) 355 (3050), 336 (3000), 319 (2680), 264 (34268), 256 (sh., 18100). Fluorescence (CHCl$_3$): $\lambda_{max}$ ($I_{rel}$)=541 (1), 572 (sh., 0.49).

| $C_{27}H_{19}NO_2$ (389.5) | Calculated | C 83.27 | H 4.92 | N 3.60 |
| --- | --- | --- | --- | --- |
| | Found | C 82.45 | H 4.69 | N 3.45 |

Example 12

N-Cyclohexylperylene-3,4-dicarboximide 0.30 g (0.93 mmol) of perylene-3,4-dicarboxylic anhydride is mixed with 0.28 g (2.8 mmol) of cyclohexylamine and 3 g of imidazole, and the mixture is heated under nitrogen at 140° C. for 3 h. The reaction product is removed from the flask by washing with ethanol, treated with 200 ml of 10% hydrochloric acid and boiled until no more ethanol is present. The residue is filtered off with suction, boiled in potassium carbonate solution and again filtered off with suction. The residue is washed with hot water until the filtrate is hardly coloured any more and then dried in a drying cabinet at 120° C. The orange shiny powder thus obtained is recrystallized twice by extraction with methanol. Yield 0.30 g (80%) of orange small crystals, strong red solid fluorescence, m.p. 370°–372° C. $R_f$ (CHCl$_3$/silica gel)=0.41. UV (CHCl$_3$): $\lambda_{max}$ ($\epsilon$)=505 (29970), 483 (30309), 354 (3160), 336 (3160), 294 (3300), 264 (29090). Fluorescence (CHCl$_3$): $\lambda_{max}$ ($I_{rel}$)=539 (1), 567 (0.51).

| $C_{28}H_{21}NO_2$ (403.5) | Calculated | C 83.35 | H 5.25 | N 3.47 |
| --- | --- | --- | --- | --- |
| | Found | C 83.28 | H 5.38 | N 3.60 |

Example 13

N-Cycloheptylperylene-3,4-dicarboximide 0.30 g (0.93 mmol) of perylene-3,4-dicarboxylic anhydride is mixed with 0.32 g (2.83 mmol) of cycloheptylamine and 3 g of imidazole, and the mixture is heated under argon at 150° C. for 4 h. The reaction product is removed from the flask by washing with ethanol, treated with 200 ml of 10% hydrochloric acid and filtered off with suction. The residue is boiled in potassium carbonate solution, filtered off with suction and washed with hot dist. water until the filtrate run-off is colourless. The product thus obtained is dried in a drying cabinet at 120° C. and then recrystallized by extraction with methanol. Yield 0.24 g (62%) of orange crystals showing a red solid fluorescence, m.p. 354°–355° C., $R_f$ (CHCl$_3$/silica gel)=0.79. UV (CHCl$_3$): $\lambda_{max}$ ($\epsilon$)=505 (30370), 483 (30967), 353 (3170), 336 (3170), 295 (3460), 264 (29047). Fluorescence (CHCl$_3$): $\lambda_{max}$ ($I_{rel}$)=529 (1), 568 (0.48).

| $C_{29}H_{23}NO_2$ (417.5) | Calculated | C 83.43 | H 5.55 | N 3.35 |
| --- | --- | --- | --- | --- |
| | Found | C 82.55 | H 5.62 | N 3.55 |

EXAMPLE 13A

N-(2,5-Di-t-butyl-4-nitrophenyl)perylene-3,4-dicarboximide 0.20 g (0.93 mmol) of perylene-3,4-dicarboxylic anhydride is mixed with 0.47 g (1.9 mmol) of 2,5-di-t-butyl-4-nitroaniline, 0.20 g of zinc acetate dihydrate and 4 g of imidazole, and the mixture is heated under argon at 170° C. for 22 h. The product is removed from the flask by washing with ethanol, treated with 2N hydrochloric acid and then boiled until all the ethanol has evaporated. The solid product is filtered off with suction, washed twice with water and then boiled in 10% potassium carbonate solution. The reaction product is again filtered off with suction while hot and washed several times with hot water until the filtrate run-off is no longer yellow. The residue is dried in a drying cabinet at 120° C. and then chromatographed on silica gel using toluene. The solution thus obtained is filtered through a D5 sintered crucible in order to remove any adhering silica gel. Yield 0.09 g (26%) of a red powder showing a red solid fluorescence, m.p. >360° C., $R_f$ (CHCl$_3$/silica gel)=0.31, UV (CHCl$_3$): $\lambda_{max}$ ($\epsilon$)=514 (24450), 489 (25850), 356 (3100), 265 (33790). Fluorescence (CHCl$_3$): $\lambda_{max}$ ($I_{red}$)=543 (1), 576 (0.45).

| $C_{36}H_{30}N_2O_4$ (554.7) | Calculated | C 77.96 | H 5.45 | N 5.05 |
| --- | --- | --- | --- | --- |
| | Found | C 77.78 | H 6.14 | N 4.85 |

EXAMPLE 14

Preparation of N-(1-hexylheptyl)perylene-3,4-dicarboximide (2c) from N-(1-hexylheptyl)perylene-9,10-dicarboximide-3,4-dicarboxylic anhydride 300 mg (0.6 mmol) of N-(1-hexylheptyl)perylene-9,10-dicarboximide-3,4-dicarboxylic anhydride and 6 ml of 12 per cent KOH are heated in an autoclave (following the procedure of Bull. Chem. Soc. Jpn. 1981, 54, 1575) at 205° C. for 22 h. After cooling, the reaction product is filtered off with suction and washed twice with water. 10 mg (4%) of dicarboximide 2c, in addition to a small amount of perylene, can be obtained from the remaining residue (20 mg) by chromatography on silica gel using chloroform.

EXAMPLES 15–18

Preparation of N-substituted Perylenedicarboximides from Perylenedicarboximide

Example 15

N-(1-Hexyl)perylene-3,4-dicarboximide a) Reaction of Perylene-3,4-dicarboximide with Hexyl Bromide and Potassium Carbonate in Dimethylformamide:

A suspension of 0.30 g (=0.93 mmol) of perylene-3,4-dicarboximide, 0.52 g (=4 mmol) of anhydrous potassium carbonate and 0.31 g (=1.86 mmol) of hexyl bromide in 20 ml of abs. dimethylformamide is prepared, and the mixture is stirred at room temperature overnight. For workup, 300 ml of water are added, the red precipitate is filtered off with suction and washed with water. According to the IR spectrum, only a very small portion of the product thus obtained is the expected N-(1-hexyl)perylene-3,4-dicarboximide, while the major portion is unreacted starting material.

b) Reaction of Perylene-3,4-dicarboximide with Hexyl Bromide and KOH in Dimethyl Sulfoxide:

A suspension of 0.16 g (=0.50 mmol) of perylene-3,4-carboximide and 0.28 g (=4.25 mmol) of potassium hydroxide pellets in 20 ml of dried dimethyl sulfoxide is prepared, and 0.33 g (=2.00 mmol) of 1-bromohexane is then added dropwise to this mixture. The mixture is stirred at room temperature for 66 h, during which a colour change from dark-red to red-brown can be observed. After the reaction is complete, 150 ml of dist. water are added, the precipitated red-brown product is then filtered off with suction and washed with saturated sodium chloride solution and dist. water. The residue is dried in a drying cabinet at 120° C. An IR spectrum shows that the product is mainly a mixture of N-(1-hexyl)perylene-3,4-dicarboximide and perylene-3,4-dicarboximide. The two products can be separated by chromatographic filtration on silica gel using chloroform, and the N-(1-hexyl)perylene-3,4-dicarboximide is then chromatographed again on silica gel using chloroform. The first fraction obtained is 20 mg of a yellow product which as shown by thin-layer chromatography is not uniform. The NMR spectrum shows that the products contain hexyl radicals, which indicate that the products are probably various perylenecarboxamides and -carboxylic esters. Because the differences in the $R_f$ values are too small, no further purification is undertaken. The second fraction obtained is 60 mg (=30%) of N-(1-hexyl)perylene-3,4-dicarboximide in the form of a red powder, m.p. >350° C. $R_f$ (CHCl$_3$/silica gel)=0.61.

Example 16

N-(1-Tetradecyl)perylene-3,4-dicarboximide 0.40 g (1.25 mmol) of perylene-3,4-dicarboximide and 0.45 g (8 mmol) of KOH powder are suspended in 30 ml of DMSO, 1.38 g of 1-bromotetradecane are added, and the mixture is stirred at room temperature for 90 h. For precipitation, 300 ml of dist. water are added, the precipitated product is filtered off with suction and washed with dist. water and dilute sodium chloride solution. Chromatographic filtration, followed by column chromatography, in each case on silica gel using chloroform, gives a yellow and a red fraction. According to thin-layer chromatography on silica gel using 3:2 xylene/petroleum ether, the yellow fraction contains 3 products having such similar $R_f$ values that no further purification is undertaken. Yield 30 mg. A colour comparison shows that the red fraction is N-(1-tetradecyl)perylene-3,4-dicarboximide. Yield 30 mg (5%) of a red powder showing a strong solid fluorescence. $R_f$ (CHCl$_3$/silica gel)=0.81.

Example 17

N-(1-Octyl)perylene-3,4-dicarboximide 0.40 g (1.25 mmol) of perylene-3,4-dicarboximide is suspended in 25 ml of abs. methanol, 0.17 g (1.87 mmol) of sodium methoxide is added, and the mixture is stirred at room temperature for 0.5 h. The solvent is then removed on a rotary evaporator, 20 ml of abs. N-methylpyrrolidone and 0.54 g (2.81 mmol) of 1-bromooctane are added to the residue, and the mixture is stirred at room temperature for 23 h. The N-methylpyrrolidone is removed on a rotary evaporator in vacuo, the red residue is flashed several times through a silica gel column 20 cm in length using chloroform. Unreacted perylene-3,4-dicarboximide is held back at the starting point, and in addition a yellow and a red fraction can be obtained. According to the NMR spectrum, the red fraction is N-(1-octyl)perylene-3,4-dicarboximide, which is subsequently recrystallized by extraction with methanol. Yield 60% of red small crystals showing red solid fluorescence.

Example 18

N-(7-tridecyl)perylene-3,4-dicarboximide 0.40 g (1.25 mmol) of perylene-3,4-dicarboximide is suspended in 25 ml of abs. methanol, 0.13 g (1.43 mmol) of sodium methoxide is added, and the mixture is stirred at room temperature for 0.5 h. The solvent is then removed on a rotary evaporator, 20 ml of abs. N-methylpyrrolidone and 0.74 g (2.80 mmol) of 7-tridecyl bromide are added to the residue, and the mixture is stirred at room temperature for 23 h. The N-methylpyrrolidone is removed on a rotary evaporator in vacuo, the red residue is flashed several times through a silica gel column 20 cm in length using chloroform. Unreacted perylene-3,4-dicarboximide is held back at the starting point, and in addition a yellow and a red fraction can be obtained. Comparison with a sample shows that the red fraction is the desired N-(7-tridecyl)perylene-3,4-dicarboximide, yield 15 mg (2.4%), while a thin-layer chromatogram (3:2 xylene/petroleum ether) shows that the yellow fraction consists of 3 products; because of the slight differences in the $R_f$ values, no further purification is undertaken.

EXAMPLE 19

Perylene-3,4-dicarboxylic acid, potassium salt 510 mg (1.0 mmol) of N-(2,5-di-tert-butylphenyl) perylene-3,4-dicarboximide (2b) and 1.4 g (18 mmol) of 85 per cent KOH are suspended in 47 ml of tert-butyl alcohol, and the suspension is boiled for 2 h with stirring. This gives a light orange solution whose colour slowly changes to yellow. Simultaneously a pure yellow precipitate of 3-carboxyl-perylene-4-N-(2,5-tert-butylphenyl) carboxamide, potassium salt (8) is formed, which is very soluble in water and exhibits an intensive yellow-green fluorescence in solution. 100 ml of 50 per cent acetic acid are added dropwise to the heated suspension of the crude reaction solution, giving a red-orange suspension, which is stirred at room temperature for another 2 h and then filtered off with suction. The red-brown solid thus obtained is dried in a drying cabinet at 120° C. and then boiled in 200 ml of 10 per cent potassium carbonate solution and washed several times with warm water until the wash water ran-off is colourless. The filtration residue essentially consists of N-(2, 5-di-tert-butylphenyl)perylene-3,4-dicarboximide (2a) (yield 27%). Upon cooling, perylene-3,4-dicarboxylic acid, potassium salt crystallizes from the aqueous phases (m.p. >250° C. UV (H20): $\lambda_{max}$ ($\epsilon$): 450 (28110), 424 (23490), 402 (sh, 11870). Fluorescence (H$_2$O, very strong) $\lambda_{max}$ (I$_{rel}$): 465 (1), 491 (0.98).

| | Calculated | C 61.16 | H 2.99 |
|---|---|---|---|
| | Found | C 60.87 | H 2.97 |

EXAMPLE 20

Perylene-3,4-dicarboxylic anhydride (4)

The combined hot aqueous phases obtained according to Example 19 are acidified with glacial acetic acid. In order to agglomerate the precipitate, it is boiled for a short period and then filtered off with suction. Yield 220 mg (67%), m.p. >260° C. Rf (CHCl$_3$/silica gel)=0.16. UV (CHCl$_3$): $\lambda_{max}$ ($\epsilon$): 472 (sh); 487 (32900); 508 (29910). Fluorescence (CHCl$_3$): $\lambda_{max}$ (I$_{rel}$)A=544 (1), 578 (0.46).

| C$_{22}$H$_{10}$O$_3$ (322.3) | Calculated | C 91.98 | H 3.12 |
|---|---|---|---|
| | Found | C 81.69 | H 3.24 |

EXAMPLES 21–22

Preparation of Perylene-3,4-dicarboxylic Ester Amides

Example 21

3-Carbomethoxy-N-(2,5-di-tert-butylphenyl)-N-methylperylene-4-carboxamide (9)

530 mg (1.04 mmol) of N-(2,5-di-tert-butylphenyl) perylene-3,4-dicarboximide (2b) are reacted to give 3-carboxy-N-(2,5-di-tert-butylphenyl)perylene-4-carboxamide, potassium salt (8), which is then dissolved in 10 ml of N-methylpyrrolidone. The reaction solution is warmed to 30° C., a mixture of 1.00 ml (3.20 mmol) of methyl iodide in 5 ml of N-methylpyrrolidone is then slowly added dropwise to the warm solution. After 48 h, the solvent is distilled off in vacuo, the residue is taken up in chloroform, the resulting mixture is filtered and chromatographed on silica gel using chloroform. The first fraction obtained is N-(2,5-di-tert-butylphenyl)perylene-3,4-dicarboximide (2a) (30 mg, 6%). The ester is obtained as the second fraction. Yield 260 mg (45%), m.p. 297°–298° C. R$_f$(CHCl$_3$/silica gel)=0.36. UV (CHCl$_3$): $\lambda_{max}$ ($\epsilon$): 459 (27940), 430 (23980), 409 (sh, 10500), 259 (30240). Fluorescence (CHCl$_3$) $\lambda_{max}$: 482, 501 (sh).

| C$_{38}$H$_{37}$NO$_3$ (555.718) | Calculated | C 82.13 | H 6.71 | N 2.52 |
|---|---|---|---|---|
| | Found | C 81.85 | H 6.90 | N 2.59 |

Example 22

3-Carbomethoxy-N-(4-tert-butylphenyl)-N-methylperylene-4-carboxamide 0.30 g (0.66 mmol) of N-(4-t-butylphenyl)perylene-3,4-dicarboximide is mixed with 0.94 g of KOH pellets, 32 ml of t-butanol are added, and the mixture is boiled for 2 h, during which a colour change from orange-red to orange can be observed. After cooling, the orange precipitate is filtered off with suction, dissolved in 20 ml of N-methylpyrrolidone, and the resulting solution is stirred together with 1 ml of methyl iodide for 2.25 h. The solvent is distilled off, and the dark-yellow residue is purified by column chromatography on silica gel using chloroform and subsequent chromatographic recrystallization from petroleum ether. Yield 0.14 g (42%) of yellow small crystals showing light red solid fluorescence, m.p. 272° C. R$_f$(ethyl acetate/silica gel)=0.74.

| C$_{34}$H$_{29}$NO$_3$ (499.6) | Calculated | C 81.74 | H 5.85 | N 2.80 |
|---|---|---|---|---|
| | Found | C 81.93 | H 5.82 | N 2.88 |

EXAMPLES 23–25

Preparation of perylene-3,4-dicarboxamidines

Example 23

Reaction of Perylene-3,4-dicarboxylic Anhydride with Neopentanediamine—Preparation of 3,3-dimethylpyrimido [2, 1 -a]benz[6, 10]anthra[2, 1,9-def]isoquinoline-6(2H,3H,4H)-one Following the method of Bull. Chem. Soc. Jpn. 1981, 54, 1575, 380 mg (1.20 mmol) of perylene-3,4-dicarboxylic anhydride are mixed with 600 mg (5.88 mmol) of neopentanediamine, 15 ml of dist. water are added, and the mixture is stirred at room temperature for 1 h. It is then refluxed for 3 h, resulting in slow formation of a red suspension. 50 ml of a 5 per cent KOH solution is added thereto, the mixture is heated to boiling once, the reaction product is filtered off with suction and washed twice with water and then with ethanol. The orange-coloured residue is dried in a drying cabinet at 120° C. and recrystallized by extraction with methanol. Yield: 320 mg (70%) of an orange-coloured powder showing red solid fluorescence, m.p. 273°–274° C. UV (CHCl$_3$) $\lambda_{max}$ ($\epsilon$)=259 nm (22400), 266 (30900), 339 (3160), 353 (2770), 484 (28100), 506 (30000). Fluorescence (CHCl$_3$): $\lambda_{max}$ (I$_{rel}$)=541 nm (1), 573 (0.80).

| C$_{27}$H$_{20}$N$_2$O (388.5) | Calculated | C 83.48 | H 5.19 | N 7.21 |
|---|---|---|---|---|
| | Found | C 82.39 | H 5.21 | N 7.39 |

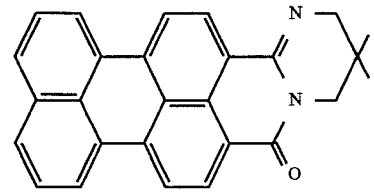

Example 24

Reaction of o-phenylenediamine with Perylene-3,4-dicarboxylic Anhydride—Preparation of Benz[6,10] anthra[2, 1,9-def]benz[3,4]imidazolo[2, 1-a] isoquinolin-7-one 400 mg (1.24 mmol) of perylene-3,4-dicarboxylic anhydride, 0.17 g of zinc acetate dihydrate, 590 mg (5.46 mmol) of o-phenylenediamine are suspended in 10 ml of quinoline, and the entire mixture is heated under argon at 210° C. for 5.5 h. At the end of the reaction, 30 ml of ethanol are added, the mixture is heated to boiling, and the reaction product is then filtered off. The dark-red-coloured product is acidified with hydrochloric acid, filtered off with suction, washed with water and then dried in a drying cabinet at 120° C. It is then recrystallized three times by extraction with toluene. Yield 480 mg of a brown-violet powder, m.p. >370° C. UV (CHCl$_3$): $\lambda_{max}$ ($\epsilon_{rel}$)=549 nm (0.55), 522 (0.71), 492 (sh, 0.49), 354 (0.17), 342 (0.16), 286 (0.75), 270 (1), 262 (0.96), 255 (0.95).

| C$_{28}$H$_{14}$N$_2$O (394.4) | Calculated | C 85.26 | H 3.58 | N 7.10 |
| | Found | C 85.43 | H 3.61 | N 7.12 |

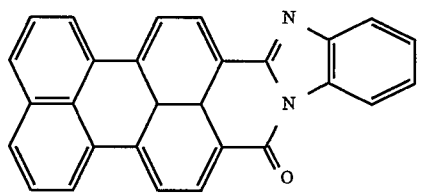

Example 25

Reaction of Perylene-3,4-dicarboxylic Anhydride with 2-amino-4-t-butylaniline Dihydrochloride Using the method of Bull. Chem. Soc. Jpn. 1981, 54, 1575 0.30 g (0.93 mmol) of perylene-3,4-dicarboxylic anhydride is mixed with 0.26 g (1.1 mmol) of 2-amino-4-t-butylaniline dihydrochloride, 5.00 g of imidazole and 0.13 g of zinc acetate dihydrate, and the mixture is heated first at 140° C. for 4 h and then at 185° C. for another 2 h. The reaction mixture is removed from the flask by washing with ethanol, treated with 200 ml of 10% hydrochloric acid and then heated until all the ethanol has evaporated. The violet precipitate is filtered off with suction, washed with dist. water and then dried in a drying cabinet at 120° C. The product is recrystallized twice by extraction with methanol. Yield 55% of a brown powder, when spread, violet. The $^1$H NMR spectrum shows that a mixture of the two possible isomers has been obtained, but the isomers are not separated. M.p. >370° C. UV (CHCl$_3$): $\lambda_{max}$ ($\epsilon$)=552 nm (sh, 24480), 525 (31592), 498 (sh, 23800), 355 (7600), 344 (7600), 327 (5000), 289 (23587), 273 (30308), 265 (sh, 27889). Fluorescence (CHCl$_3$): $\lambda_{max}$ (I$_{rel}$)=546 nm (sh, 0.13), 593 (1).

| C$_{32}$H$_{22}$N$_2$O (450.5) | Calculated | C 85.31 | H 4.92 | N 6.22 |
| | Found | C 84.16 | H 4.88 | N 6.13 |

Example 25A

Reaction of perylene-3,4-dicarboxylic anhydride with 2,3-diamino-naphthalene -preparation of benz [6,10]anthra[2, 1,9-def]naphthyl[3,4]imidazolo[2,1-a]-isoquinolin-7-one 0.25 g (0.78 mmol) of perylene-3,4-dicarboxylic anhydride is mixed with 0.25 g (1.56 mmol) of 2,3-diaminonaphthalene, 0.10 g of zinc acetate dihydrate in 10 ml of quinoline, and the mixture is heated under argon at 200° C. for 2.5 hours. The quinoline is distilled off in vacuo, the residue is removed by washing with ethanol and treated with 2N hydrochloric acid. The ethyl alcohol is evaporated off, the dark precipitate is filtered off with suction and then washed several times with hydrochloric acid and water. The residue is boiled in 2N potassium carbonate solution, filtered off, washed with water and then dried in a drying cabinet at 120° C. The violet, very sparingly soluble crystalline powder thus obtained is recrystallized four times by extraction with toluene and then dried in a drying cabinet at 120° C. Yield 0.28 g (81%), m.p. >360° C. UV (CHCl$_3$): $\lambda_{max}$ ($\epsilon$)=570 nm (0.128), 533 (0.198), 514 (0.201), 484 (0.16), 381 (0.083), 359 (0.089), 324 (0.106), 312 (0.117), 264 (0.401). Fluorescence (CHCl$_3$): $\lambda_{max}$ (I$_{rel}$)=541 nm (1), 585 (0.57).

| C$_{32}$H$_{16}$N$_2$O (444.6) | Calculated | C 86.47 | H 3.63 | N 6.30 |
| | Found | C 82.65 | H 3.69 | N 6.28 |

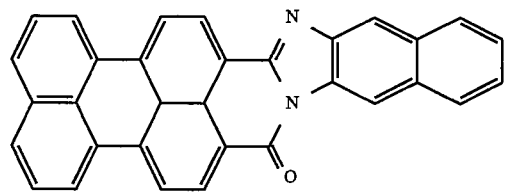

EXAMPLES 26–26A

Preparation of Perylene-3,4-dicarboxylic Diesters

Example 26

Dimethyl Perylene-3,4-dicarboxylate 0.20 g (0.62 mmol) of perylene-3,4-dicarboxylic arthydride and 0.05 g (0.93 mmol) of sodium methoxide are suspended in 8 ml of abs. methanol, and the suspension is stirred at room temperature for 0.5 h, during which its colour changes from brown to yellow. The solvent is removed on a rotary evaporator, 10 ml of N-methylpyrrolidone and 0.09 ml (1.4 mmol) of methyl iodide are added to the residue, and the mixture is stirred at room temperature for 48 h. 50 ml of water are added to the orange-yellow solution, the precipitated product is then filtered off with suction and dried in a drying cabinet at 120° C. According to the thin-layer chromatogram (CHCl$_3$/silica gel) the yellow product thus obtained is almost clean. It is separated off from a rapidly moving product by chromatographic filtration on silica gel using chloroform and then washed off the silica gel with ethyl acetate. Yield 0.18 g (79%), m.p. 256°–257° C. R$_f$ (CHCl$_3$/silica gel)=0.07. UV (CHCl$_3$): $\lambda_{max}$ ($\lambda$)=460 nm (25920), 438 (23925), 340 (1920), 329 (1910), 260 (31217). Fluorescence (CHCl$_3$, exc. 489 nm) $\lambda_{max}$ (I$_{rel}$)=483 nm (1), 507 (0.81). MS (70 eV): m/z (%)=370 (3.65), 369 (23.59), 368 (M$^+$, 100), 338 (10.68), 337 (M$^+$—CH$_3$O, 46.20), 323 (8.69), 322 (M$^+$—CH$_3$O—CH$_3$, 36.35), 294 (11.65), 278 (11.79), 250 (23.13), 238 (9.73), 237 (7.77), 168 (9.21), 125 (13.73).

Example 26A

Dipropyl Perylene-3,4-dicarboxylate 0.18 g (0.56 mmol) of perylene-3,4-dicarboxylic anhydride is suspended in 10 ml of dried n-propanol, 0.15 g (1.43 mmol) of potassium t-butoxide is added, and the suspension is stirred at room temperature for 0.5 hour with the exclusion of moisture. During the course of the reaction, a colour change from brown to yellow can be observed, during which the precipitate dissolves. The solvent is then distilled off, and first 10 ml of N-methylpyrrolidone and then 0.20 ml (2.4 mmol) of 1-bromopropane are added, and the yellow solution is stirred at room temperature for 17 hours. The solvent is distilled off in vacuo, the yellow residue is chromatographed on silica gel using chloroform. Yield 0.16 g (68%), m.p. 253° C., $R_f$(CHCl$_3$/silica gel)=0.48. UV (CHCl$_3$): $\lambda_{max}$ ($\epsilon$)=460 nm (27944), 437 (23875), 340 (1900), 327 (2050), 260 (32991). Fluorescence (CHCl$_3$):$\lambda_{max}$ ($I_{rel}$)=482 nm (1), 509 (0.69), solid fluorescence: $\lambda_{max}$=595 nm.

| $C_{28}H_{24}O_4$ (424.5) | Calculated | C 79.23 | H 5.70 |
|---|---|---|---|
| | Found | C 79.32 | H 5.98 |

EXAMPLES 27–31

Nitration of the Perylene-3,4-dicarboximides

Example 27

Nitration of N-(1-hexylheptyl)perylene-3,4-dicarboximide with Acetic Tinhydride/nitric Acid 120 mg (240 mmol) of N-(1-hexylheptyl)perylene-3,4-dicarboximide are suspended (following the method of Acta. Chim. Scand 1983, B37, 65) in 1 ml of acetic anhydride, and a mixture of 0.057 ml of conc. nitric acid in 0.15 ml of acetic anhydride is added at 0° C. After 2 h, the mixture is allowed to warm slowly to room temperature, and stirring is continued for another 72 h. The dark-red product is evaporated in vacuo, and the residue is chromatographed on silica gel using chloroform. According to the $^1$H NMR (CDCl$_3$), the first fraction obtained is a mixture of 60 % of N-(1-hexylheptyl)perylene-3,4-dicarboximide and 40% of N-(1-hexylheptyl)-2-nitroperylene-3,4-dicarboximide, but these compounds cannot be separated by chromatography ($R_f$ value 0.85; chloroform/silica gel). According to the $^1$H NMR (CDCl$_3$), the second fraction eluted is N-(1-hexylheptyl)-9-nitroperylene-3,4-dicarboximide.

Example 28

9-Nitro-N-(1-hexylheptyl)percene-3,4-carboximide (10)

500 mg (1.00 mmol) of N-(1-hexylheptyl)perylene-3,4-dicarboximide are dissolved in 100 ml of dichloromethane, and 2.9 ml of a solution of nitrogen dioxide in dichloromethane (15.7 g of NO$_2$ per liter, 1.00 mmol) is added in complete darkness (exclusion of daylight!). The mixture is then allowed to stand at room temperature for 17.75 h in the absence of light, and the dichloromethane is then evaporated off on a rotary evaporator. A thin-layer chromatogram (chloroform/silica gel) shows that the residue obtained consists mainly of 2 compounds having $R_f$ values of 0.89 and 0.73. The substance having the higher $R_f$ value is unreacted starting material, 210 mg (42%) of which can be recovered by column chromatography (chloroform/silica gel). The 2nd chromatography fraction is purified by extractive recrystallization from methanol. Yield 300 mg (55%) of wine-red needles (the structure is proven by $^1$H NMR, COSY and NOESY spectra). M.p. 184°–185° C. $R_f$ (chloroform/silica gel)=0.73. UV (CHCl$_3$): $\lambda_{max}$ ($\epsilon$)=510 nm (34344), 483 nm (30844), 357 nm (broad, 4470). Fluorescence (CHCl$_3$): $\lambda_{max}$=549 nm.

| $C_{35}H_{36}N_2O_4$ (548.7) | Calculated | C 76.62 | H 6.61 | N 5.11 |
|---|---|---|---|---|
| | Found | C 76.60 | H 6.58 | N 5.41 |

Example 29

Nitration of N-(2,5-di-tert-butylphenyl)perylene-3,4-dicarboximide with N$_2$O$_4$ with Exposure to Light 250 mg (0.49 mmol) of N-(2,5-di-tert-butylphenyl)perylene-3,4-dicarboximide are dissolved (following the method of Acta. Chim. Scand. 1983, B37, 65) in 17 ml of dichloromethane with exposure to daylight, and 1.5 ml of a solution of NO$_2$ in dichloromethane containing 15.7 g/l (0.5 mmol) are then added. After a reaction time of 17 h at room temperature, the solvent is evaporated off on a rotary evaporator. A thin-layer chromatogram (chloroform/silica gel) shows that the residue obtained consists mainly of 3 dyes having $R_f$ values of 0.27, 0.38 and 0.49, the compound having the $R_f$ value of 0.38 being the starting material, as shown by comparison with an authentic sample. The crude product is chromatographed on silica gel using chloroform, which allows 80 mg (32%) of N-(2,5-di-tert-butylphenyl)perylene-3,4-dicarboximide to be recovered. The compound having an $R_f$ value of 0.49 could be obtained in pure form by chromatographing it several times on silica gel using chloroform and then recrystallizing it by extraction with methanol and can be identified by $^1$H, COSY and NOESY NMR spectra as 1-nitro-N-(2,5-di-t-butylphenyl)perylene-3,4-dicarboximide. Yield 20 mg (7%), m.p. 331°–335° C. (dec.). $R_f$ (chloroform/silica gel)=0.49. UV (CHCl$_3$): $\lambda_{max}$ ($\epsilon$): 514 (25290), 409 (broad, 4350), 356 (broad, 6250).

| $C_{36}H_{30}N_2O_4$ (554.6) | Calculated | C 77.96 | H 5.45 | N 5.05 |
|---|---|---|---|---|
| | Found | C 77.17 | H 5.64 | N 4.84 |

Example 30

Nitration of N-(1-hexylheptyl)perylene-3,4-dicarboximide with N$_2$O$_4$ with Exposure to Light and Methanesulfonic Acid Catalysis 430 mg (0.85 mmol) of N-(2,5-di-tert-butylphenyl)perylene-3,4-dicarboximide are dissolved (following the method of Acta. Chim. Scand. 1983, B37, 65) in 25 ml of dichloromethane, and 10 μl of methanesulfonic acid are added to the red solution. 5 ml of a solution of 15.7 g of dinitrogen tetroxide in one liter of dichloromethane (0.85 mmol) are then added dropwise to this solution, which immediately changes its colour to wine-red. The solution is allowed to stand overnight, and the dichloromethane is then evaporated off on a rotary evaporator. A thin-layer chromatogram (chloroform/silica gel) of the wine-red residue shows the formation of 4 main products and a few by-products. The residue is chromatographed on silica gel using chloroform, which enables all 4 main products to be obtained in pure form. The following fractions are obtained one after the other:

1st fraction: 60 mg of a wine-red powder which is further purified by extraction with ethyl acetate and repeated chromatography on silica gel using chloroform. Yield 30 mg (5%) of 1,6-dinitro-N-(1-hexylheptyl)perylene-3,4-carboximide (identified by NMR and MS spectra), m.p.

142°–144° C., $R_f$(chloroform/silica gel)=0.81. UV (CHCl$_3$): $\lambda_{max}$=508, 482. Fluorescence (CHCl$_3$): $\lambda_{max}$ ($I_{rel}$)=541 (1), 573 (sh, 0.72).

| C$_{35}$H$_{35}$N$_3$O$_6$ (593.7) | Calculated | C 70.81 | H 5.94 | N 7.08 |
|---|---|---|---|---|
|  | Found | C 70.88 | H 5.94 | N 6.61 |

2nd fraction: contaminated 9-nitro-N-(1-hexylheptyl) perylene-3,4-carboximide.

3rd fraction: 0.22 g of a wine-red substance which according to the $^1$H NMR spectrum consists of 81% of 9-nitro-N-(1-hexylheptyl)perylene-3,4-dicarboximide and 19% of 2,5-dinitro-N-(1-hexylheptyl)perylene-3,4-dicarboximide. However, these two compounds cannot be obtained in pure form either by column chromatography on silica gel using chloroform or toluene or by fractional crystallization from acetonitrile or other solvents.

4th fraction: 130 mg of a dark-red substance which is recrystallized by extraction with methanol. This gives 90 mg (25%) of dark-red crystals which can be identified by a $^1$H and a NOESY NMR spectrum as 9,10-dinitro-N-(1-hexylheptyl)perylene-3,4-dicarboximide, m.p. 245°–246° C. $R_f$(chloroform/silica gel)=0.54. UV (CHCl$_3$): $\lambda_{max}$ ($\epsilon$)= 506 nm (58015), 474 (40792), 446 (16730).

| C$_{35}$H$_{35}$N$_3$O$_6$ (593.7) | Calculated | C 70.81 | H 5.94 | N 7.08 |
|---|---|---|---|---|
|  | Found | C 70.65 | H 5.78 | N 7.38 |

Example 31

Nitration of N-(2,5-di-t-butylphenyl)perylene-3,4-dicarboximide with NO$_2$ in the Absence of Light 0.75 g (1.47 mmol) of N-(2,5-di-t-butylphenyl)perylene-3,4-dicarboximide is dissolved (following the method of Acta. Chim. Scand. 1983, B37, 65), in 30 ml of abs. dichloromethane, and 6.94 ml (1.48 mmol) of a solution containing 19.5 g/l of NO$_2$ in dichloromethane are added in the absence of light. The red solution is allowed to stand at room temperature overnight and is then evaporated on a rotary evaporator. A thin-layer chromatogram on silica gel using chloroform shows the presence of 3 compounds having $R_f$ values of 0.43, 0.32 and 0.18. The compound having the $R_f$ value of 0.32 is the starting material, as shown by comparison with a sample. The compound having the $R_f$ value of 0.43 can be obtained in pure form by repeated flash chromatography on silica gel (0.04–0.063 mm) using chloroform, followed by extractive recrystallization from methanol and can be identified by $^1$H, COSY and NOESY NMR spectra as 1-nitro-N-(2,5-di-t-butylphenyl)perylene-3,4-dicarboximide. Yield 0.08 g (10%) of a wine-red powder, m.p. >335° C. $R_f$(chloroform/silica gel)=0.43. UV (CHCl$_3$): $\lambda_{max}$ ($\epsilon$): 511 (27690), 409 (broad, 5105), 357 (broad, 7170), 267 (26710).

| C$_{36}$H$_{30}$N$_2$O$_4$ (554.6) | Calculated | C 77.96 | H 5.45 | N 5.05 |
|---|---|---|---|---|
|  | Found | C 77.95 | H 5.33 | N 4.87 |

The compound having the $R_f$ value of 0.18 can be isolated by fractional flash chromatography on silica gel (0.04–0.63 mm) using chloroform and by recrystallizing it twice by extraction with ethyl acetate and can be identified by $^1$H, COSY and NOESY NMR spectra as 9-nitro-N-(2,5-di-t-butylphenyl)perylene-3,4-dicarboximide. Yield 0.26 g (32%) of a red powder, slight orange solid fluorescence. M.p. >365° C., $R_f$(CHCl$_3$/silica gel) 0.18. UV (CHCl$_3$) $\lambda_{max}$ ($\epsilon$): 512 (35590), 484 (32104), 358 (4920), 347 (4680), 262 (30924), 255 (29495). Fluorescence (CHCl$_3$) $\lambda_{max}$ ($I_{rel}$): 549.

| C$_{36}$H$_{30}$N$_2$O$_4$ (554.6) | Calculated | C 77.96 | H 5.45 | N 5.05 |
|---|---|---|---|---|
|  | Found | C 77.31 | H 5.36 | N 5.16 |

Furthermore, 0.27g (36%) of N-(2,5-di-t-butylphenyl) perylene-3,4-dicarboximide can be recovered.

EXAMPLE 32

9-Acetamido-N-(1-hexylheptyl)perylene-3,4-dicarboximide 100 mg (0.18 mmol) of 9-nitro-N-(1-hexylheptyl) perylene-3,4-dicarboximide (10) are suspended in 15 ml of glacial acetic acid, 80 mg (0.72 mmol) of iron dust are then added, and the red suspension is refluxed for 4.5 h, during which a slow colour change from red to red-brown and purple and then to dark-purple can be observed. First water is added to the cooled, violet solution, and the reaction mixture is then neutralized with 10 per cent KOH. The suspension which is now reddish purple is extracted three times with chloroform, the combined organic phases are dried with anhydrous sodium sulfate then evaporated on a rotary evaporator. According to the thin-layer chromatogram (chloroform/silica gel), the purple-coloured product obtained consists of 2 main products having $R_f$ values of 0.02 and 0.43. This product is filtered by chromatography on silica gel using chloroform until the solution leaving the silica gel is no longer violet. The red-coloured silica gel is extracted with chloroform to give, after evaporation on a rotary evaporator, 50 mg of a red powder which is then recrystallized by extraction with methanol. Yield: 30 mg (30%) of 9-acetamido-N-(1-hexylheptyl)perylene-3,4-dicarboximide, m.p. >230° C.; from 172°–175° C. onwards product turns brown. Rf (CHCl$_3$/glacial acetic acid 20:1; silica gel)=0.90. UV (CHCl$_3$): $\lambda_{max}$ ($\epsilon$)=506 nm (31589, broad), 356 (2995). Fluorescence (CHCl$_3$): $\lambda_{max}$=574 nm (broad).

| C$_{37}$H$_{40}$N$_2$O$_3$ (560.7) | Calculated | C 79.25 | H 7.19 |
|---|---|---|---|
|  | Found | C 77.66 | H 7.27 |

EXAMPLE 33

9-Amino-N-(1-hexylheptyl)perylene-3,4-dicarboximide (17)

100 mg (0.18 mmol) of 9-nitro-N-(1-hexylheptyl) perylene-3,4-dicarboximide and 70 mg of iron powder are suspended in 30 ml of ethanol and 2 ml of conc. hydrochloric acid is then slowly added. The mixture is refluxed for 1 h, during which a colour change to yellow-brown can be observed. The mixture is neutralized with KOH, the dark residue is filtered off with suction and dried in a drying cabinet at 120° C. A thin-layer chromatogram (chloroform/silica gel) shows that 2 substances having $R_f$ values of 0.21 and 0.32 have been formed. They are chromatographed on silica gel using chloroform to give 10 mg of a blue-coloured powder as the first fraction. According to the NMR and mass spectra, it probably consists of two azo compounds having very high mass numbers. The second fraction is 9-amino- N-(1-hexylheptyl)perylene-3,4-dicarboximide, yield 80 mg (85%) of a blue powder, m.p. 211° C., $R_f$ (chloroform/silica gel)=0.20. UV (CHCl$_3$): $\lambda_{max}$ ($\epsilon$)=554 nm (27940), 375 (4903), 356 (5412), 277 (29123), 262 (23798). Fluorescence (CHCl$_3$): $\lambda_{max}$=642 nm (weak).

EXAMPLE 34

9-N,N-Dimethylamino-N'-(1-hexylheptyl)perylene-3,4-carboximide:

190 mg (0.37 mmol) of 9-amino-N'-(1-hexylheptyl) perylene-3,4-carboximide are mixed with 2 g of formic acid, and 40 mg of 37% aqueous formaldehyde solution are then added. The suspension is heated at 75°–80° C. for 18 h, during which a colour change from red to blue can be observed. The violet product is precipitated by adding 20 ml of 50% KOH solution. Stirring is continued for 1 h, the product is then filtered off with suction, washed with water and dried in a drying cabinet. Repeated chromatography of the product on silica gel using chloroform enables 2 substances having $R_f$ values of 0.92 and 0.51 to be isolated. The substance having the higher $R_f$ value can be identified by $^1$H NMR spectroscopy as 9-N,N-dimethylamino-N'-(1-hexylheptyl)perylene-3,4-carboximide (70 mg=39%), while the substance having the smaller $R_f$ value is identified by comparison of the thin-layer chromatograms and the $^1$H NMR spectra as the starting material (40 mg=48%). Yield: 70 mg (39%), m.p.: 168°–169° C. UV (CHCl$_3$): $\lambda_{max}$ ($\epsilon$)=542 (26400), 506 sh (21000), 382 (3000), 357 (3200), 269 (25800), 262 (25700). Fluorescence (CHCl$_3$): $\lambda_{max}$ (I$_{rel}$)=662.

| $C_{37}H_{42}N_2O_2$ (546.8) | | | | |
|---|---|---|---|---|
| Calculated | C 81.28 | H 7.74 | N 5.12 | |
| Found | C 80.96 | H 7.67 | N 5.04. | |

EXAMPLES 35–36

Bromination of the perylene-3,4-dicarboximides

Example 35

9-Bromo-N-(1-hexylheptyl)perylene-3,4-carboximide (18c)

10 mg (1.0 mmol) of N-(1-hexylheptyl)perylene-3,4-dicarboximide (2c) are dissolved (following the method of Dyes and Pigments 1991, 16, 19) in 70 ml of chlorobenzene, the solution is heated to 40° C., and a solution of 100 gl (4 mmol) of bromine in 10 ml of chlorobenzene is rapidly added to the orange solution which immediately changes its colour to wine-red. The solution is stirred at 40°–50° C. for 2.5 h, and the chlorobenzene is then evaporated off on a rotary evaporator. A thin-layer chromatogram (toluene/silica gel) shows the presence of 4 products, one of which having an $R_f$ value of 0.77 is the main product. The residue is chromatographed 8 times on silica gel using toluene to give 30 mg (7%) of N-(1-hexylheptyl)perylene-3,4-dicarboximide. The pure yellow product which is isolated as the forerun comprises poly-(di- to penta-)brominated N-(1-hexylheptyl)-perylene-3,4-dicarboximides as shown by the mass spectrum. The compounds cannot be separated by chromatography. The main fraction is recrystallized by extraction with pentune. Yield 310 mg (65%) of an orange powder which shows a strong solid fluorescence, m.p. 186°–187° C. $R_f$ (chloroform/silica gel)=0.77. UV (CHCl$_3$): $\lambda_{max}$ ($\epsilon$)=508 (35675), 484 (33985). Fluorescence (CHCl$_3$) $\lambda_{max}$ (I$_{rel}$)=540 (1), 568 (sh, 0.49). The position of the bromine atom can be elucidated by combination of $^1$H, NOESY and COSY NMR spectra.

| $C_{35}H_{36}NO_2Br$ (582.6) | | | | |
|---|---|---|---|---|
| Calculated | C 72.16 | H 6.23 | N 2.40 | Br 13.72 |
| Found | C 72.13 | H 6.31 | N 2.63 | Br 12.88 |

Example 36

9-Bromo-N-(2,5-di-tert-butylphenyl)perylene-3,4-dicarboximide (18b)

650 mg (1.28 mmol) of N-(2,5-di-tert-butylphenyl) perylene-3,4-dicarboximide (2b) are dissolved in 100 ml of chlorobenzene, the red solution is mixed with 650 mg of anhydrous potassium carbonate, and 0.30 ml of bromine in 10 ml of chlorobenzene is then added dropwise to the mixture. The reaction mixture is stirred at 40°–50° C. for 2 h, the temperature is then increased to 50°–60° C. and maintained there for another 5 h, and the chlorobenzene is then evaporated off on a rotary evaporator, during which substantial amounts of bromine are also removed. A thin-layer chromatogram (toluene/silica gel) shows that no more starting material is present in the residue obtained, which could only be removed with difficulty. Several separations by column chromatography on silica gel using chloroform afford 610 mg of an orange powder which is recrystallized by extraction with ethyl acetate. Yield 570 mg (77%) of orange-coloured small needles having a slight solid fluorescence, m.p. >320° C. $R_f$(CHCl$_3$/silica gel)=0.43. UV (CHCl$_3$): $\lambda_{max}$ ($\epsilon$)=511 nm (36058), 486 (35564), 357 (3430). Fluorescence (CHCl$_3$): $\lambda_{max}$ (I$_{rel}$)=542 nm (1), 572. The position of the bromine substituent could be determined by comparison with the spectrum of 9-bromo-N-(1-hexylheptyl)perylene-3,4-dicarboximide and $^1$H spectra. The substitution pattern of the comparison substance was determined by a combination of COSY and NOESY spectra.

| $C_{36}H_{30}NO_2Br$ (588.6) | | | | |
|---|---|---|---|---|
| Calculated | C 73.47 | H 5.14 | N 2.38 | Br 13.58 |
| Found | C 73.54 | H 5.32 | N 2.40 | Br 13.19 |

(A small mount of another red substance can be obtained from the prefraction in pure form according to the thin-layer chromatogram (chloroform/silica gel) by repeated column chromatography on silica gel using chloroform. The mass spectrum shows a molecular weight of 667 having the typical isotope pattern of 3 bromine atoms. However, the substance has a UV/visible absorption and fluorescence spectrum which is quite similar to that of 9-bromo-N-(2,5-di-tert-butylphenyl)perylene-3,4-dicarboximide, indicating that the chromophore must have been retained in any case).

EXAMPLE 37: Solvatochromism of 9-amino-N'-(7-tridecyl)perylene-3,4-dicarboximide The abovementioned compound shows a marked solvatochromism in selected solvents arranged according to increasing polarity (for example according to the ET$_{30}$ scale), in that not only the UV but also the fluorescence absorption maximum undergoes a batochromic shift with increasing polarity of the solvent. This can be seen, for example, from the corresponding values in toluene compared with ethanol:

| Toluene: | UV $\gamma_{max}$ = 550 nm; | Fluorescence $\gamma_{max}$ = 631 nm |
| Ethanol: | UV $\gamma_{max}$ = 608 nm; | Fluorescence $\gamma_{max}$ = 713 nm |

EXAMPLE 38

Pigment Properties of N-(2,5-di-t-butylphenyl)perylene-3,4-dicarboximide and N-cyclooctylperylene-3,4-dicarboximide The compounds mentioned prepared according to Example 1 and Example 7, respectively are used to colour polyethylene terephthalate (Melinar®890, ICI) in a concentration of 0.03%. The brilliant orange colorations are heat-resistant at 300° C. for 5 minutes; they show no migration in PVC according to DIN 53775 (24 h, 80° C.); and have excellent light stability according to ISO 105-A02 (5 on the grey scale after 500 h).

What is claimed is:

1. A process for preparing a perylene-3,4-dicarboximide of the formula I

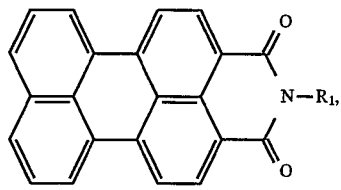

(I)

in which $R_1$ is a $C_1$-$C_{41}$alkyl; aralkyl; cycloalkyl containing 3–12 carbon atoms in the ring; substituted or unsubstituted aryl containing 6–12 carbon atoms; or aromatic heterocycle selected from the group consisting of furyl, thienyl, pyrrolyl, imidazolyl, pyrazolyl, isothiazolyl, isoxazolyl, pyridyl, pvrazinyl, pyrimidinyl, pyridazinyl, indolyl, isoindolyl, indazolyl, quinolyl, isoquinolyl, and carbozolyl, by reacting perylene-3,4,9,10-tetracarboxylic dianhydride with a primary amine $R_1$-$NH_2$ at a temperature of 150°–350° C. and under pressure, in the presence of water and in the presence of a zinc salt, lead salt, calcium salt or magnesium salt and of a nitrogen-containing heterocycle as the base.

2. A process according to claim 1, in which the salt is lead acetate, zinc chloride or zinc acetate.

3. A process according to claim 1, in which the nitrogen-containing heterocycle is quinoline, pyridine or imidazole.

4. A process according to claim 2, in which the salt is zinc acetate.

5. A process according to claim 3, in which the nitrogen-containing heterocycle is imidazole.

6. A process according to claim 1, wherein $R^1$ is 2,5-di-tert-butylphenyl, 4-tert-butylphenyl, 2,3-dimethylphenyl, 1-hexylheptyl, 1-octylnonyl, 1-nonyldecyl, cyclopropyl, cyclopentyl, cyclohexyl, cycloheptyl, cyclooctyl, cyclododecyl, adamantyl or 4-carbamoylphenyl.

* * * * *